(12) United States Patent
Koehler et al.

(10) Patent No.: US 9,730,663 B2
(45) Date of Patent: Aug. 15, 2017

(54) UNCERTAINTY MAPS FOR SEGMENTATION IN THE PRESENCE OF METAL ARTIFACTS

(75) Inventors: Thomas Koehler, Norderstedt (DE);
Holger Schmitt, Hamburg (DE);
Heinrich Schulz, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1529 days.

(21) Appl. No.: 12/673,779

(22) PCT Filed: Aug. 12, 2008

(86) PCT No.: PCT/IB2008/053236
§ 371 (c)(1),
(2), (4) Date: Feb. 17, 2010

(87) PCT Pub. No.: WO2009/027889
PCT Pub. Date: Mar. 5, 2009

(65) Prior Publication Data
US 2011/0038516 A1    Feb. 17, 2011

Related U.S. Application Data (60) Provisional application No. 60/969,176, filed on Aug. 31, 2007.

(51) Int. Cl.
*G06K 9/00* (2006.01)
*A61B 6/00* (2006.01)
(Continued)

(52) U.S. Cl.
CPC .............. *A61B 6/5258* (2013.01); *G06T 7/11* (2017.01); *G06T 7/149* (2017.01);
(Continued)

(58) Field of Classification Search
CPC ........ A61B 6/5258; G06T 2207/10081; G06T 2207/20012; G06T 2207/30052
(Continued)

(56) References Cited

U.S. PATENT DOCUMENTS 6,047,080 A * 4/2000 Chen et al. ................... 382/128
6,507,633 B1    1/2003 Elbakri et al.
(Continued)

FOREIGN PATENT DOCUMENTS

| WO | 2005076222 A1 | 8/2005 |
|---|---|---|
| WO | 2006039809 A1 | 4/2006 |
| WO | 2008084352 A1 | 7/2008 |

OTHER PUBLICATIONS

Weese, J., et al. "Shape Constrained Deformable Models for 3D Medical Image Segmentation", Lecture Notes on Computer Science, 2001, vol. 2082, pp. 380-387.*
(Continued)

*Primary Examiner* — Robert Sorey (57) ABSTRACT

When performing model-based segmentation on a 3D patient image (80), metal artifacts in the patient image (80), caused by metal in the patient's body, are detected, and a metal artifact reduction technique is performed to reduce the artifact(s) by interpolation projection data in the region of the artifact(s). The interpolated data is used to generate an uncertainty map for artifact-affected voxels in the image, and a mesh model (78) is conformed to the image to facilitate segmentation thereof. Internal and external energies applied to push and pull the model (78) are weighted as a function of the uncertainty associated with one or more voxels in the image (80). Iteratively, mathematical representations of the energies and respective weights are solved to describe an updated model shape that more closely aligns to the image (80).

20 Claims, 10 Drawing Sheets (51) Int. Cl.
*G06T 7/11* (2017.01)
*G06T 7/149* (2017.01)

(52) U.S. Cl.
CPC ........... *G06T 2207/10081* (2013.01); *G06T 2207/20012* (2013.01); *G06T 2207/30052* (2013.01)

(58) Field of Classification Search
USPC ........................................ 382/128
See application file for complete search history.

(56) References Cited

U.S. PATENT DOCUMENTS

| | | | |
|---|---|---|---|
| 6,631,212 B1* | 10/2003 | Luo et al. | 382/228 |
| 6,721,387 B1 | 4/2004 | Naidu et al. | |
| 2005/0123197 A1* | 6/2005 | Tank | 382/173 |
| 2005/0249431 A1* | 11/2005 | Ruhmschopf | 382/274 |
| 2008/0085040 A1* | 4/2008 | Basu et al. | 382/128 |
| 2008/0095300 A1* | 4/2008 | Zingelewicz et al. | 378/4 |
| 2008/0170791 A1* | 7/2008 | Eskildsen et al. | 382/199 |
| 2008/0253635 A1* | 10/2008 | Spies et al. | 382/131 |
| 2008/0260230 A1* | 10/2008 | Gotardo et al. | 382/131 |
| 2010/0069741 A1* | 3/2010 | Kuhn et al. | 600/424 |
| 2010/0074538 A1* | 3/2010 | Mishra et al. | 382/224 |

OTHER PUBLICATIONS

Gu, J., et al.; Metal Artifacts Reduction in CT Images through Euler's Elastica and Curvature Based Sinogram Inpainting; 2006; SPIE Int'l. Soc. for Optical Engineering; vol. 6144 III; pp. 614465-1.

Weese, J., et al.; Shape Constrained Deformable Models for 3D Medical Image Segmentation; 2001; Lecture Notes on Computer Science; vol. 2082:380-387.

Zhang, Y., et al.; Reducing Metal Artifacts in Cone-Beam CT Images by Preprocessing Projection Data; 2007; Int. J. Radiation Oncology Biol. Phys.; 67(3)924-932.

\* cited by examiner

UNCERTAINTY MAPS FOR SEGMENTATION IN THE PRESENCE OF METAL ARTIFACTS

CROSS REFERENCE TO RELATED APPLICATIONS

This application claims the benefit of U.S. provisional application Ser. No. 60/969,176 filed Aug. 31, 2007, which is incorporated herein by reference.

The present application finds particular application in model-based segmentation systems, particularly involving adaptive subject imaging. However, it will be appreciated that the described technique may also find application in other subject imaging systems, other image adaptation scenarios, or other medical techniques.

Metal implants such as hip replacements or dental fillings are a source of severe artifacts in CT imaging. A prominent and undesirable effect is that metal implants cause beam-hardening, which causes dark and bright shades close to and radiating from the metal. Metal artifacts impede proper diagnosis, as well as automatic or semi-automatic organ segmentation. Metal artifact reduction methods can improve subjective image quality for the observer. Regardless of the visual improvement, these methods are often based on removal of the artifacted voxels and replacement by an interpolation of nearby voxels, which introduces an additional uncertainty, such that that there is no guarantee that original structures are recovered by the method. Moreover, structures are often unaccounted for after metal artifact reduction, and other structures may be undesirably introduced. This imposes another impediment for automatic organ segmentation.

Image reconstruction and/or segmentation can be detrimentally affected by metal in a patient. In one example of model-based reconstruction, a mesh model of an organ is superimposed on a diagnostic image or diagnostic data. Two opposing forces, internal energy through which the model tries to hold its shape, and external energy that urges the model towards the interfaces or surfaces in the diagnostic image, work concurrently in opposition to bring the model to the shape of the organ. While model-based segmentation is satisfactory when the edges of the organ are well-defined in the image, problems can arise when there is artifact degradation, such as the metal artifacts discussed above. That is, metal objects (e.g., pins, screws, hip replacements, filings, etc.) in a patient create artifacts, such as streaks, which obscure image detail, increasing uncertainty regarding the exact location of the surface of the organ.

The present application provides new and improved model-based segmentation systems and methods that account for uncertainty associated with image data obscured by metal artifacts, which overcome the above-referenced problems and others.

In accordance with one aspect, a system for system for image segmentation in the presence of metal artifacts includes a model generator that receives patient image data and stores trained models of anatomical structures, and a voxel analyzer that determines whether metal artifacts are present in one or more voxels in the patient image data. The system further includes a processor that executes a metal artifact reduction algorithm and generates an uncertainty map with corrected voxel data incorporated therein for a patient image generated from the patient image data, and a segmentation tool that conforms a trained model of an anatomical structure corresponding to the patient image and segments the patient image using a model-based segmentation technique and evaluates the uncertainty derived by the processor.

In accordance with another aspect, a method for performing model-based segmentation in includes generating a patient image of a region of a patient that includes a metal object, generating an uncertainty map for the patient image indicative of uncertainty in portions of the patient image due to metal object reconstruction artifacts, and employing the uncertainty map when segmenting a portion of the patient image displaced from the metal object using model-based segmenting.

In accordance with another aspect, an apparatus that facilitates model-based segmentation using uncertainty maps includes means for generating patient image data, means for reconstructing the patient image data into a 3D patient image, and means for detecting metal artifacts in one or more voxels in the 3D patient image. The apparatus further includes means for generating an uncertainty map with interpolated data that reduces the metal artifacts, means for weighting features associated with regions of a surface of a mesh model, and means for segmenting the 3D patient image using model-base segmentation to conform the mesh model to the 3D patient image.

In accordance with another aspect, a method of performing model-based segmentation comprises generating a diagnostic image of an organ or region of a subject, which image has metal artifacts, selecting a model of the imaged organ or region, and applying a first force on the model, which urges the model to hold its initial shape. The method further comprises applying a second force on the model, which urges the model to deform into alignment with corresponding interfaces in the diagnostic image, and, on an image voxel by image voxel basis, adjusting the first and second forces in accordance with the degree of metal artifacting, such that the magnitude of the first force relative to the second force increases for voxels with a higher degree of metal artifacting, and the magnitude of the second force relative to the first force increases for voxels with a lower degree of metal artifacting.

Yet another aspect relates to a system for image segmentation in the presence of metal artifacts, including a model generator that receives patient image data and stores trained models of anatomical structures, a voxel analyzer that determines whether metal artifacts are present in one or more voxels in the patient image data, and a processor that generates an uncertainty map without changing the patient image data. The system further includes a segmentation tool that conforms a trained model of an anatomical structure corresponding to the patient image and segments the patient image using a model-based segmentation technique and evaluates the uncertainty derived by the processor.

One advantage is that image segmentation accuracy is improved.

Another advantage resides in mitigating metal artifact distortion in segmented images.

Another advantage resides in reducing total energy expended to deform a model to an image, which improves processing speed.

Still further advantages of the subject innovation will be appreciated by those of ordinary skill in the art upon reading and understand the following detailed description.

The innovation may take form in various components and arrangements of components, and in various steps and arrangements of steps. The drawings are only for purposes of illustrating various aspects and are not to be construed as limiting the invention.

FIG. 8 illustrates an example of an internal force instruction in execution, such as may be executed or prompted by the segmentation tool in conjunction with a CT scanner or the like.

The systems and methods described herein facilitate segmenting an image of soft tissue whose surface boundaries are artifacted and rendered uncertain by artifacts from a metal object in other regions of an imaged subject. For example, a metal ball in a hip replacement can cause a starburst-like artifact across an image of a patient's pelvic region, partially obscuring organs of interest (e.g., bladder, prostate, etc.). Not only does the metal project artifacts into remote areas of the image, the artifact obscures the precise position of the metal itself. To improve image appearance, others have proposed trying to identify the exact location of the metal object, using this information to estimate a correction to the unreconstructed data, and reconstructing the corrected data. This and other techniques remove all or most of the starburst-like artifacts and display a reduced or substantially unartifacted image. However, due to the uncertainty associated with the identification of the true size and location of the metal object, and uncertainties in other parts of the correction process, there remains uncertainty regarding the accuracy of the boundary surfaces of the remote organs in other parts of the image. The technique(s) described herein control or adjust for the uncertainty regarding the true location of the boundary surfaces of the remote organs during segmentation of these remote organs. In a first described embodiment, the remote organs are segmented by overlaying a mesh model having the shape of a normal organ. Opposing forces are applied to the mesh model. One force is applied to move the surface of the mesh model into alignment with surface boundaries in the image. The other force is applied to hold the mesh in the nominal organ shape. The relative magnitudes of these forces are adjusted in accordance with the uncertainty. It will be appreciated that this embodiment is applicable to uncertainties due to other factors, and does not require performing a metal artifact correction technique as a preliminary step.

Figure 1:
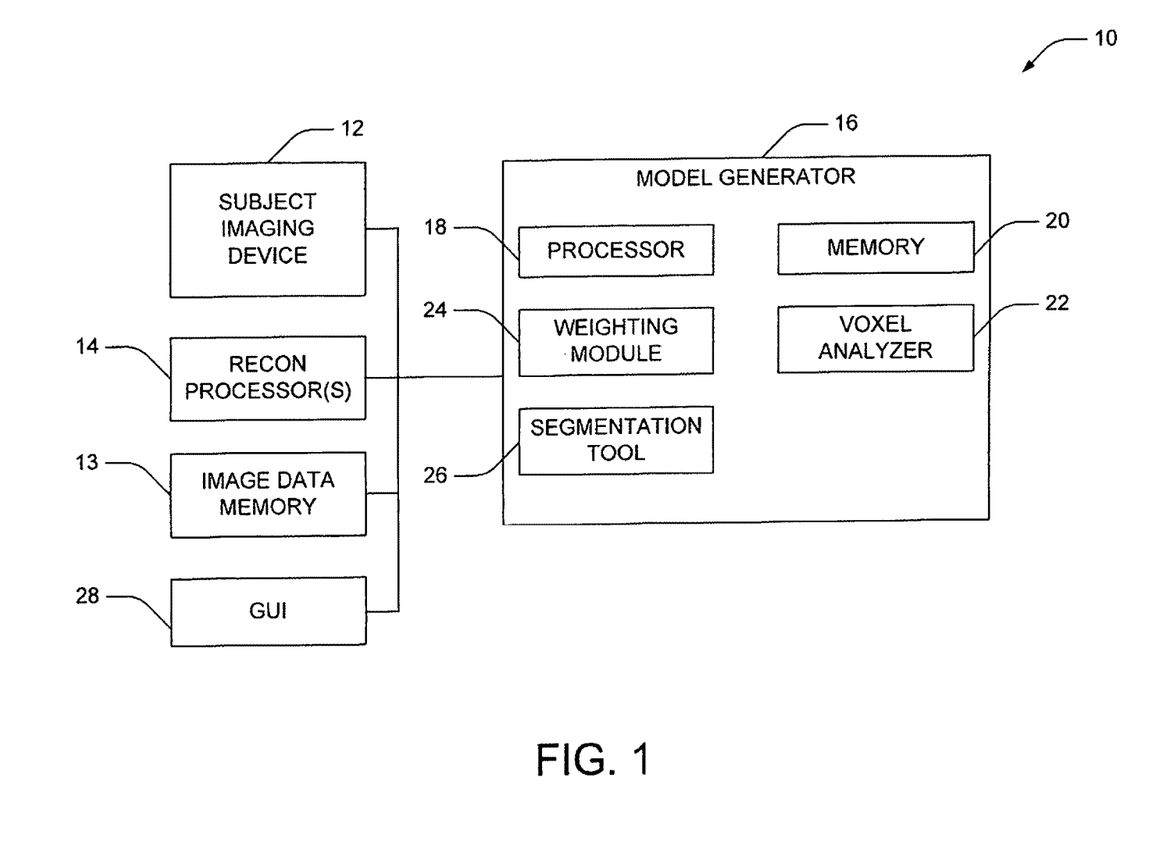
FIG. 1 illustrates a system that adjusts the external energy applied to deform an image in accordance with the likelihood that a voxel in the image is contaminated by metal artifacts.

Now turning to FIG. 1, a system 10 is illustrated, which adjusts the external energy applied to deform an image in accordance with the likelihood that a voxel in the image is contaminated by metal artifacts. The system includes a subject imaging device (SID) 12 that is coupled to an image data memory 13 and a reconstruction processor 14, which receives captured data from the SID and reconstructs the data into an image. The SID can be, for instance, a computed tomography (CT) scanner, a positron emission tomography (PET) scanner, a single photon emission computed tomography (SPECT) scanner, a magnetic resonance imaging (MRI) device, a functional MRI (fMRI) device, or some other suitable subject imaging device. The system further includes a model generator 16, which comprises a processor 18 and memory 20. The memory can store information associated with one or more models of anatomical structures, which may be generated from one or more clinical images of subjects. For instance, the memory can store 3D models of individual organs or other structures (e.g., heart, liver, kidney, bladder, prostate, lung, salivary gland, etc.), as well as groups of organs and/or structures (e.g., liver-and-kidney, heart-and-lung(s), pelvic region, abdominal region, thoracic region, cranial region, etc.). The stored models are models of the organ or structure for a nominal person and may further include models for the inter-patient variability of these organs. The model generator further includes a voxel analyzer 22 that quantitatively and qualitatively analyzes a subject image for artifacts caused by metal in the subject (e.g., fillings, hip replacements, pins, screws, etc.), and a weighting module 24 that weights the external energy locally at a voxel position according to the likelihood metal artifacts being present at this location. Furthermore, the model generator includes a segmentation tool 26 that applies external and internal forces to a selected model to conform the model to the subject image for segmentation while accounting for artifacts caused by metal objects. Additionally, the system comprises a graphical user interface (GUI) 28, which presents image and/or model information to a user and into which a user enters information to manipulate images, models, etc.

A metal identification protocol is applied by the processor 18, in conjunction with the SID 12, to identify the location of the metal. Once the metal is identified, the voxel analyzer 22 qualitatively predicts whether each voxel is contaminated by the metal artifacts. The greater the likelihood that a voxel is contaminated by metal artifacts, the more the external energy is reduced by the weighting module 24. In this manner, the shape of the model becomes the predominant force where there is increased uncertainty regarding voxels of the diagnostic image.

In another embodiment, the techniques for locating the metal objects in the image also provide for removing the metal image and removing the artifacts from the image. In this scenario, the artifacts are removed by estimating or guessing which structure should replace the artifact. For example, metal artifacts can be removed by deconstructing the image into sinograms, replacing data in the sinograms in the metal shadow by interpolated data, and reconstructing the image. Thus, the artifact-corrected images can contain uncertainties, although the uncertainties are distributed differently than in the artifact contaminated image.

According to an example, a selected organ model with a triangulated mesh surface, and a set of adaptation parameters is selected from the memory 20. When the model generator receives a data set from the SID and/or the reconstruction processor, (e.g., a CT image, MR image, 3D anatomical image, etc.), the processor executes an objective function $E_{total} = w_{int} \times E_{int} + w_{ext} \times E_{ext}$, wherein $E_{total}$ is total energy, $E_{int}$ is internal energy, $E_{ext}$ is external energy, $w_{int}$ is an internal energy weight, $w_{ext}$ is an external energy weight. The external energy is $$E_{ext} = \sum_{t=1}^{t=N_\Delta} r(\hat{x}_t) w_t (\tilde{x}_t - \hat{x}_t)^2$$

where $r(\hat{x}_t)$ represents the reliability of the external energy or force (e.g., a fraction of original data contributing locally to the image) and is spatially variant, $N_\Delta$ is the number of triangles in the mesh surface, $w_t$ is the feature strength of a triangle t, $\tilde{x}_t$ is the coordinates of the best feature for triangle t, and $\hat{x}_t$ is the coordinates of the center of triangle t.

In one embodiment, scaling the objective function ($E_{total}$) does not change the location of the minimum $(1/w_{ext}) \times E_{total} = (w_{int}/w_{ext}) \times E_{int} + E_{ext}$. Therefore, $w_{ext}$ can be set to 1 without constraining the problem, and the objective function becomes: $E_{total} = w_{int} \times E_{int} + E_{ext}$.

Figure 2:
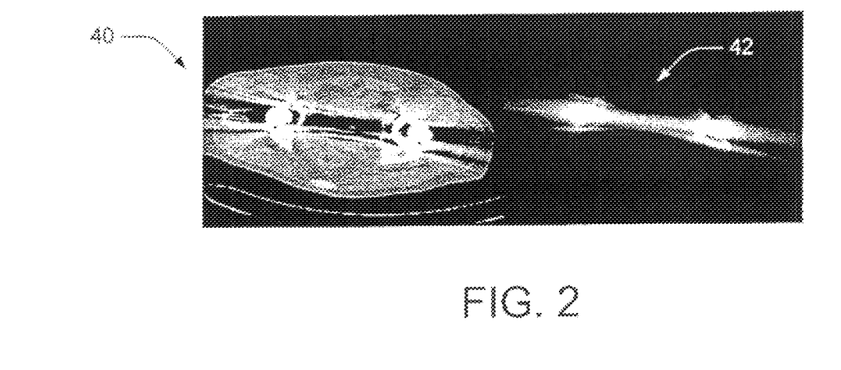
FIG. 2 illustrates an image of a hip with two implants, and an uncertainty map such as may be generated by the voxel analyzer.

FIG. 2 illustrates an image of a hip with two implants, and an uncertainty map such as may be generated by the voxel analyzer. From the image 40, and/or as a byproduct of a metal artifact reduction method or technique, an uncertainty measure is derived, which is passed forward to the GUI and/or to the segmentation tool. If segmentation is done on the original images, a method by Watzke and Kalender (Eur Radiol 14:849-856, 2004), to estimate qualitatively the likelihood that a voxel suffers from beam-hardening, can be employed. That method involves metal identification and removal of metal artifacts, which in turn includes forward projection of the metal, superlinear weighting (e.g. cubic), and unweighted back-projection. The resulting image is represented by the uncertainty map 42. The structure of the image in map 42 correlates well with the appearance of metal artifacts in the original image 40. The uncertainty map can now be used to balance locally the weight of the image term and the model term in a model based segmentation of the image 40.

Figure 3:
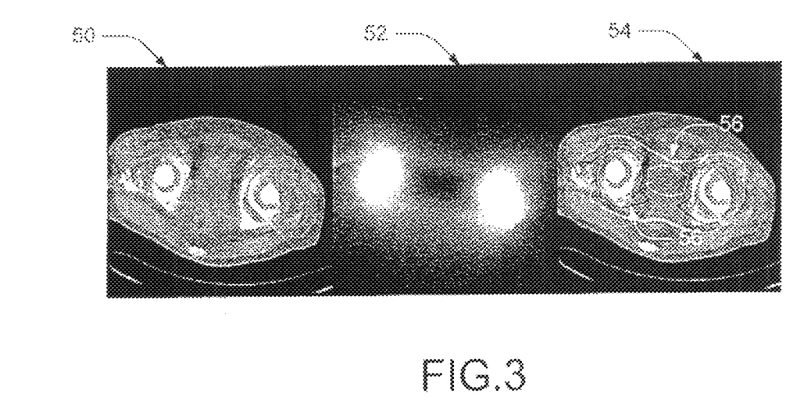
FIG. 3 shows an example of the technique as applied to the example of FIG. 2, together with a metal artifact reduction method

FIG. 3 shows an example of the technique as applied to the example of FIG. 2, together with a metal artifact reduction method (e.g., such as is described in Koehler, "Apparatus, method, and computer program for producing a corrected image of a region of interest from acquired projection data," EP07100081, filed on Jan. 4, 2007). The method involves an interpolation of projection data across the shadow of the metal. Here, the uncertainty for the image 50 can be modeled for each voxel as the fraction of interpolated projection samples that contributed to the voxel. In a more advanced scenario, both images 40 and 50 (original and corrected) can be used in the segmentation process together with the corresponding uncertainty maps 52. In addition to the image 50, which shows the original image after a metal artifact reduction method is applied, and the uncertainty map 52, image 54 shows uncertainties marked with iso-lines 56.

Figure 4:
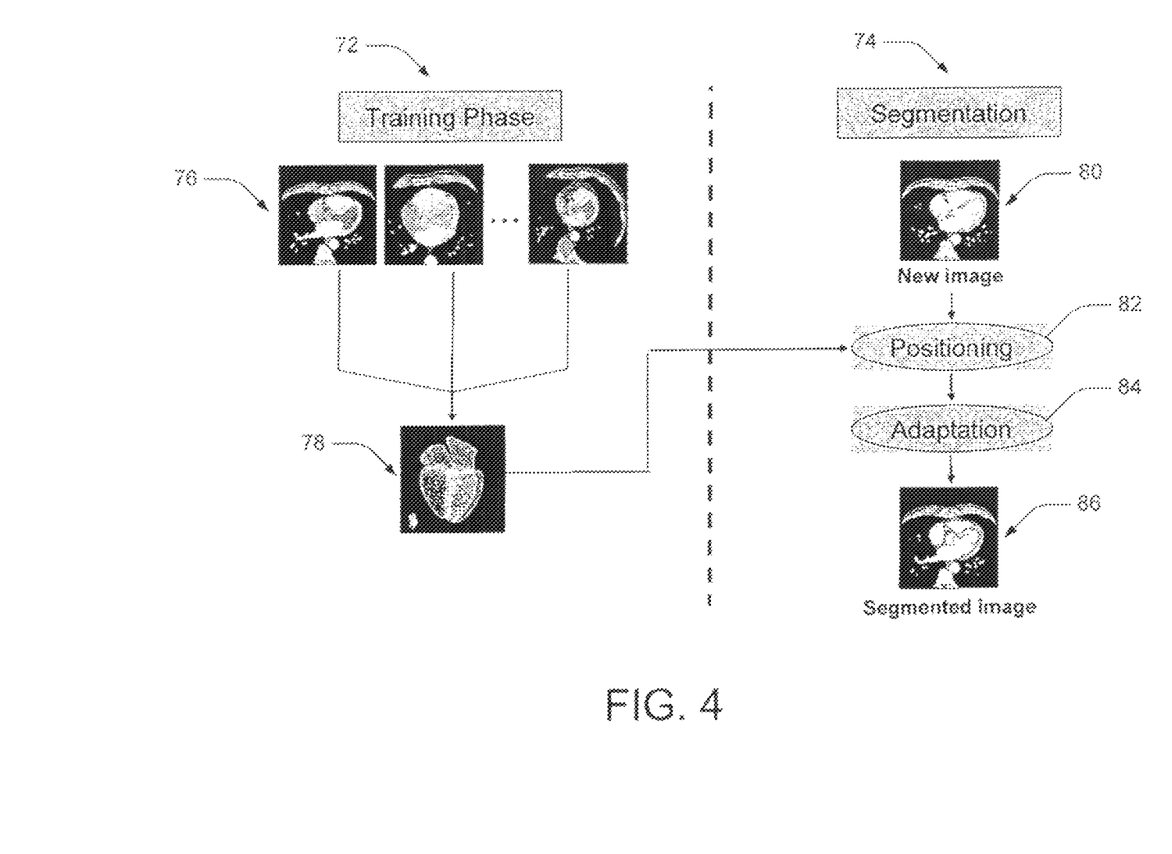
FIG. 4 illustrates a diagram of the basic principles of model-based segmentation.

FIG. 4 is a diagram illustrating some of the basic principles of model-based segmentation. Model-based segmentation includes a training phase 72 and a segmentation phase 74, which may occur sequentially and/or concurrently. During the training phase, training data 76 comprising a reference set of segmented images and corresponding mesh models is compiled, analyzed, and/or processed to generate one or more trained models 78. Each trained model has a mean mesh, shape variability, and identified features (e.g., contours, surface landmarks, etc.) at its boundaries. During the segmentation phase, a new 3D image 80 is received (e.g., at the model generator 16, etc.), such as a reconstructed image (e.g., CT, PET, SPECT, MRI, fMRI, etc.) Positioning of the new image 80 relative to the trained model 78 is performed at 82. At 84, the new image is adapted to the model (e.g., by applying internal and external forces), and the segmented image 86 is generated. The segmented model may then be employed for one or more therapy planning or the like (e.g., radiation therapy, ablation therapy, surgery, etc.)

Figure 5:
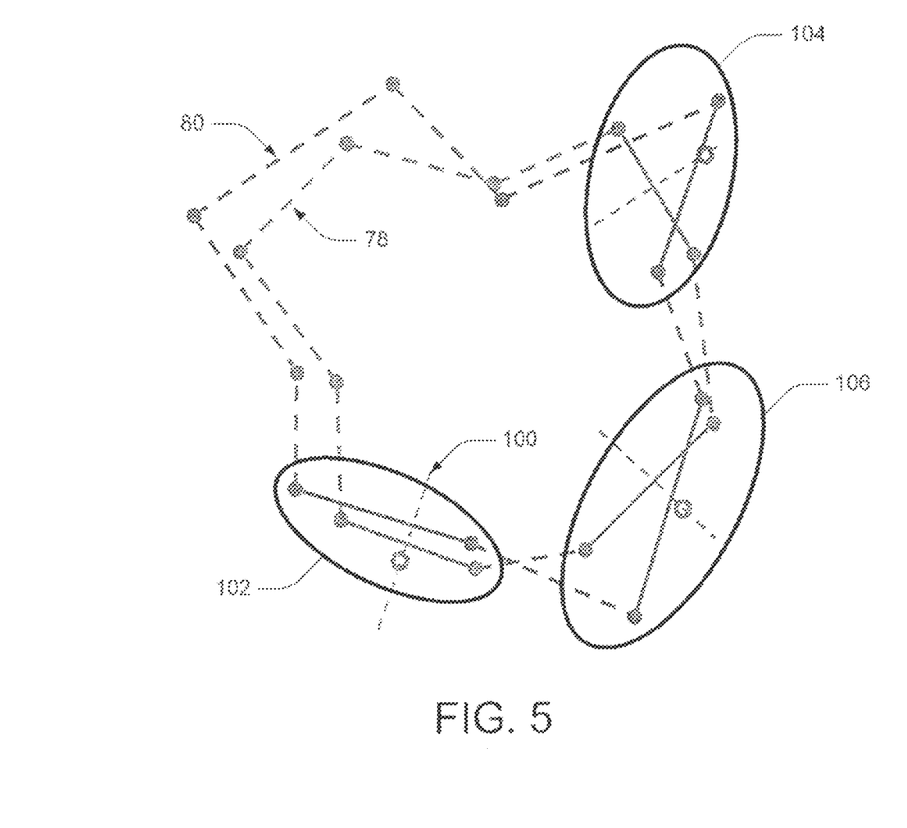
FIG. 5 is an example of segmented image adaptation of the image and a trained model using external forces that push inward on the model to adapt the model to the image.

FIG. 5 is an example of segmented image adaptation of the image 80 and a trained model 78 using external forces 100 that push inward on the model to adapt the model to the image. The external force energy is characterized by the features of the dataset (e.g., gradients), organ-model-specific adaptation parameters (e.g., maximum gradient), the shape of the mesh (e.g., normal vector of triangles in the mesh), etc.

As illustrated, a feature 102 is weak (e.g., in terms of external energy) since the features of the model and image are substantially parallel and aligned, and a reconfigured mesh does not intersect a best feature, thus the external energy applied to the feature 102 is small. Feature 104 has a large external energy contribution since the reconfigured mesh intersects the best feature of the image. Feature 106 has a moderate external energy contribution because the reconfigured mesh is near the best feature in this region.

External energy is determined by the equation:

$$E_{ext} = \sum_{t=1}^{t=N_\Delta} r(\hat{x}_t) w_t (\tilde{x}_t - \hat{x}_t)^2,$$

where $E_{ext}$ is external energy, $N_\Delta$ is the number of triangles in the mesh surface, $w_t$ is the feature strength of a triangle t, $\tilde{x}_t$ is the coordinates of the best feature for triangle t, and $\hat{x}_t$ is the coordinates of the center of triangle t.

Figure 6:
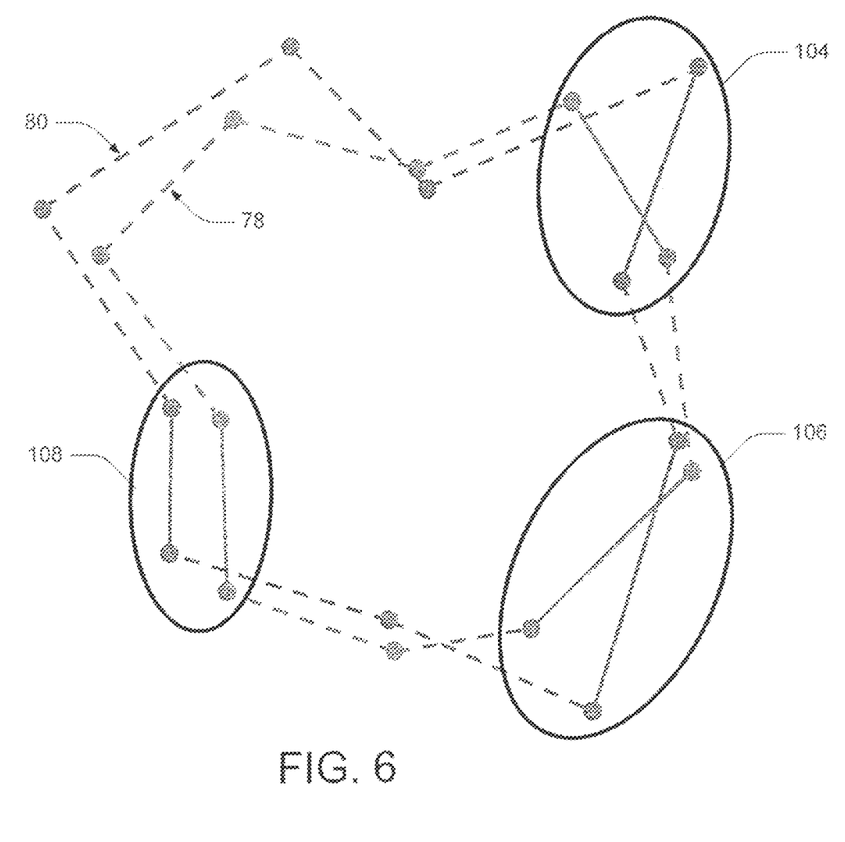
FIG. 6 shows features of the model and their associations with features of the image, which delineate the internal energies of the respective features.

FIG. 6 shows features of the model 78 and their associations with features of the image 80, which delineate the internal energies of the respective features. The internal energy of the system is characterized by the shape of the mesh (e.g., the more the mesh deforms, the greater the increase in internal energy), the shape of the model of the anatomical structure, or mean model (e.g., when the mesh and the mean model have the same shape, the internal energy is zero), and the transformation (e.g., scaling factor and rotation vector) used to register the mean mesh and current configuration of the mesh. In the figure, feature 104 has a large internal energy contribution, since the model and the image intersect each other. Feature 106 has a moderate internal energy contribution, and FIG. 108 has a low internal energy contribution.

Internal energy is mathematically described as:

$$E_{int} = \sum_{e=1}^{e=N_{edges}} (\vec{x}_e - sR\vec{x}_e^0)^2,$$

wherein $E_{int}$ is internal energy, $N_{edges}$ is the number of edges in the mesh, $\vec{x}_e$ is a vector representing edge e, s is a mean mesh scaling factor, R is the mean mesh rotation vector, and $\vec{x}_e^0$ is a mean mesh vector representing edge e.

Figure 7:
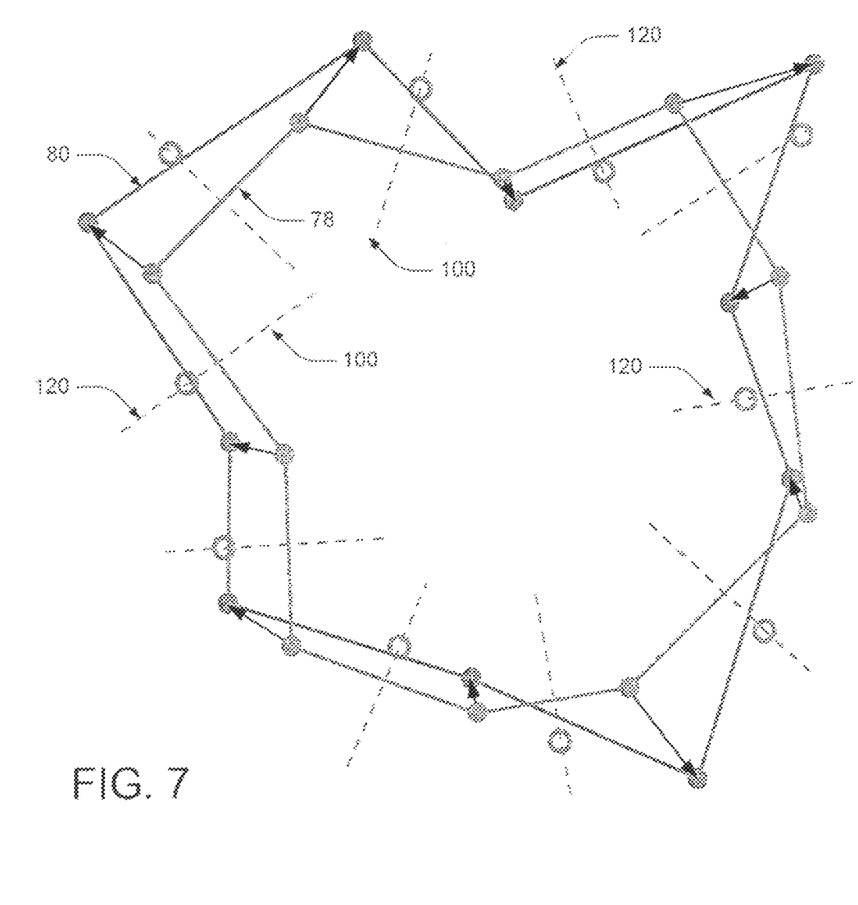
FIG. 7 illustrates an adaptation iteration wherein the mesh model is adapted to the image. It is to be appreciated that model-based segmentation is an iterative algorithm.

FIG. 7 illustrates an adaptation iteration wherein the mesh model is adapted to the image. It is to be appreciated that model-based segmentation is an iterative algorithm. At each iteration, the system assigns a "best feature" and a feature weight to each triangle of the mesh. The external energies 100 and internal energies 120 are computed using the best features and weights. Mathematically, the external and internal energies are represented by a set of equations. The set of equations is solved (e.g., a matrix is inverted), and the solution of the system of equations is the new configuration (shape) of the mesh. In FIG. 7, arrows illustrate movement of mesh model nodes toward corresponding image nodes.

Figure 8:
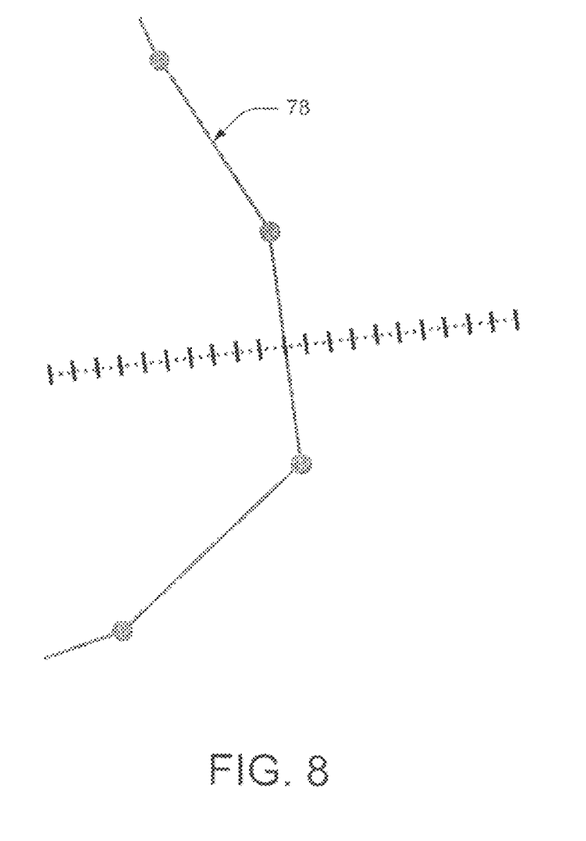

FIG. 8 illustrates an example of an internal force instruction in execution on a model 78, such as may be executed or prompted by the segmentation tool 26 in conjunction with a CT scanner or the like. According to the example, an instruction such as "take 21 steps along the triangle normal vector" (e.g., from 10 mm inside the mesh to 10 mm outside the mesh) is executed. At each step, the interpolated CT value and the gradient vector are computed. The CT values and gradient vectors are sufficient information for the model-based segmenting system to operate.

Figure 9:
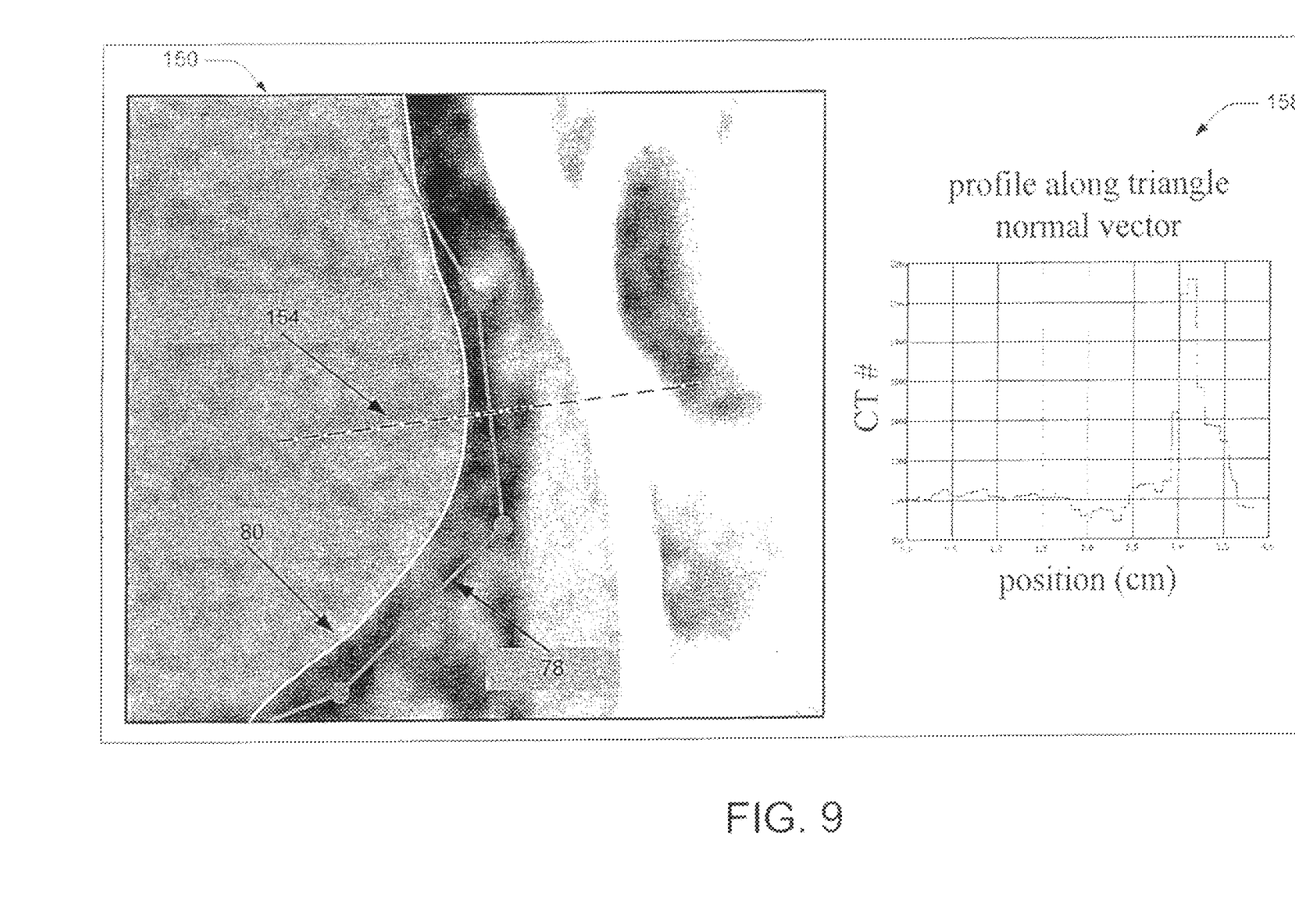
FIG. 9 is an illustration of a screenshot showing an organ surface with a mesh model surface overlaid thereon.

FIG. 9 shows a screenshot 150 showing an organ surface 80 with a mesh model 78 surface overlaid thereon. A triangle normal vector 154 extends perpendicularly through a triangle of the mesh model surface. If internal or external energies warrant, the mesh model surface at this triangle will be moved along the triangle normal vector. In the example of FIG. 9, external forces can push the mesh triangle through which the triangle normal vector passes toward the organ surface. A graph 158 of profile data along the triangle normal vector illustrates relative positions of pixels related to CT data points.

Figure 10:
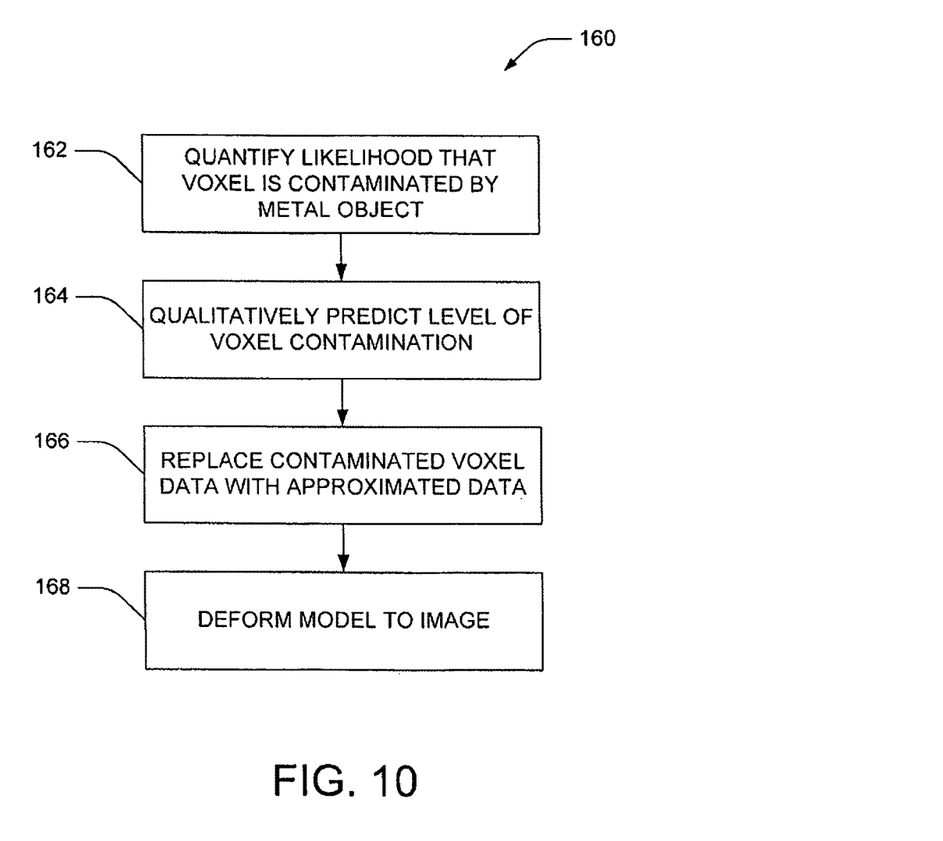
FIG. 10 illustrates a method for generating uncertainty maps in to mitigate distortion caused by metal objects in a patient when segmenting a nuclear or radiographic image of the patient.
Figure 11:
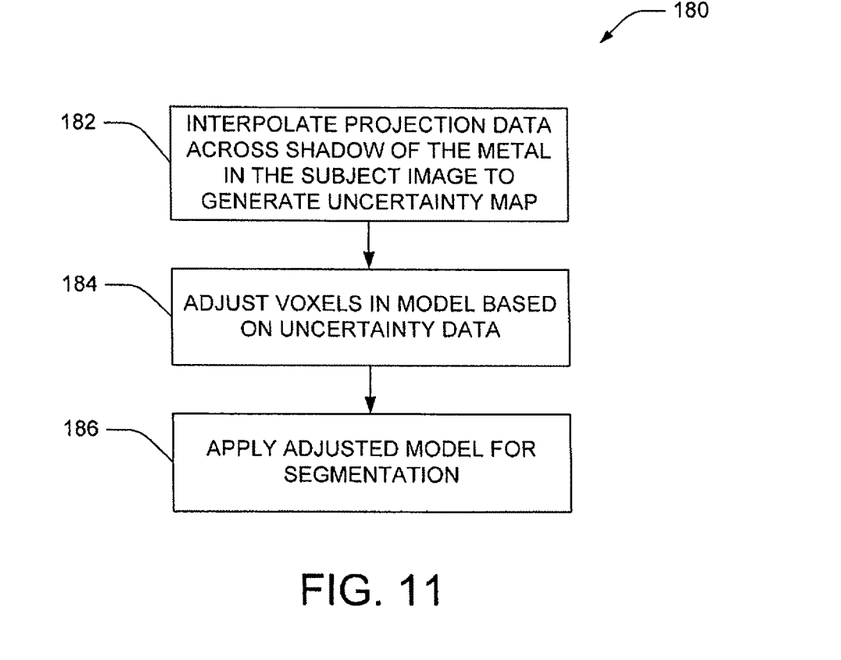
FIG. 11 illustrates a method of generating an uncertainty map to adapt a model of an anatomical structure for segmenting a patient image.

FIGS. 10-11 illustrate one or more methods related to generating uncertainty maps and compensating for distortion and/or artifacts in patient images caused by metal in the patient, in accordance with various features. While the methods are described as a series of acts, it will be understood that not all acts may be required to achieve the described goals and/or outcomes, and that some acts may, in accordance with certain aspects, be performed in an order different that the specific orders described.

FIG. 10 illustrates a method 160 for generating uncertainty maps to mitigate incorrect segmentation results caused by metal objects and corresponding artifacts in a patient when segmenting a radiographic image of the patient. At 162, the likelihood that a voxel in a patient image is contaminated by a metal artifact is quantified. In one embodiment, the quantification includes determining whether metal is present in an imaged region of the patient. At 164, a level of likelihood of metal artifact being present (e.g., beam-hardening) is qualitatively predicted. In one embodiment, the qualitative prediction is performed using a method set forth in Watzke and Kalender (Eur Radiol 14:849-856, 2004), which describes a combination of linear interpolation of reprojected metal traces and multi-dimensional adaptive filtering of raw data in conjunction with directional weighting to reduce metal artifacts. In this approach, the likelihood of metal artifacts appearance due to beam-hardening is estimated by metal identification and artifact removal, which includes forward projection, super-linear weighting (e.g. quadratic of cubic) followed by unfiltered back-projection.

At 166, contaminated voxel data is replaced with interpolated data in an uncertainty map of the patient image. The updated model is then deformed to the image using model-based segmentation to segment the image, at 168.

FIG. 11 illustrates a method 180 of generating an uncertainty map to adapt a model of an anatomical structure for segmenting a patient image. At 182, projection data is interpolated across a shadowed area caused by a metal object in a patient to facilitate generating an uncertainty map. In one embodiment, the interpolation is performed using a method described in Koehler, "Apparatus, method, and computer program for producing a corrected image of a region of interest from acquired projection data," EP07100081, filed on Jan. 4, 2007. At 184, voxels are adjusted in the model to reflect the interpolated data. For instance, each voxel is adjusted proportionally to the fraction of interpolated projection samples that contribute to the voxel, relative to the original non-interpolated samples that contribute to the voxel. At 186, the adjusted model is applied to the patient image for model-based segmentation such as is described with regard to preceding figures.

Having thus described the preferred embodiments, the invention is now claimed to be:

1. A system for image segmentation in the presence of metal artifacts, including:
   a model generator that receives patient image data and stores trained models of anatomical structures;
   a voxel analyzer that determines whether metal artifacts are present in one or more voxels in the patient image data;
   a processor that executes a metal artifact reduction algorithm and generates an uncertainty map with corrected voxel data incorporated therein for a patient image generated from the patient image data, wherein the uncertainty map indicates a likelihood of metal contamination for corrected voxels representing boundary surfaces of one or more remote organs in other parts of the patient image; and
   a segmentation tool that:
      conforms a trained model of an anatomical structure corresponding to the patient image;
      segments the patient image using a model-based segmentation technique; and
      evaluates the uncertainty map derived by the processor;
   wherein the segmentation tool applies an internal force along a surface normal vector in a surface region in which the feature is located; and
   wherein the segmentation tool applies an external force along the vector; and
   wherein the internal force increases and the external force decreases as a function of an increase in the likelihood of metal contamination associated with each corrected voxel.

2. The system according to claim 1, wherein the model has a triangulated mesh surface.

3. The system of claim 1, wherein a feature on the surface of the model is selected at least one of automatically or in response to user input.

4. The system according to claim 1, wherein the segmentation tool balances the internal force and the external force to align the surface region to a surface of the patient image.

5. The system according to claim 1, wherein the total energy applied to the feature through the internal and external forces is expressed as $E_{total} = w_{int} \times E_{int} + w_{ext} \times E_{ext}$, wherein $E_{total}$ is total energy, $E_{int}$ is internal energy, $E_{ext}$ is external energy, $w_{int}$ is an internal energy weight, and $w_{ext}$ is an external energy weight, and wherein $$E_{ext} = \sum_{t=1}^{t=N_\Delta} r(\hat{x}_t) w_t (\tilde{x}_t - \hat{x}_t)^2,$$

where $r(\hat{x}_t)$ represents the reliability of the external energy and is spatially variant, $N_\Delta$ is the number of triangles in the mesh surface, $w_t$ is the feature strength of a triangle t, $\tilde{x}_t$ is the coordinates of the best feature for triangle t, and $\hat{x}_t$ is the coordinates of the center of triangle t.

6. The system according to claim 5, wherein $w_{ext}$ is 1, and wherein the segmentation tool applies increased internal force to compensate for a detected metal artifact.

7. The system according to claim 1, wherein the model generator includes:
- a routine for determining whether a voxel is affected by a metal artifact;
- a routine for quantitatively predicting a level to which the voxel is affected by the metal artifact;
- a routine for interpolating projection data and updating the voxel with the interpolated projection data; and
- a routine for deforming the model to the patient image.

8. A method of performing model-based segmentation in the system of claim 1, including:
- determining whether a voxel is affected by a metal artifact;
- quantitatively predicting a level to which the voxel is affected by the metal artifact;
- interpolating projection data and updating the voxel with the interpolated projection data; and
- deforming the model to the patient image.

9. A processor for performing model-based segmentation, the processor being configured to:
- receive a patient image of a region of a patient that includes a metal object;
- generate an uncertainty map for the patient image indicative of a likelihood of metal contamination of corrected voxels in the patient image due to metal object reconstruction artifacts;
- segment the patient image;
- employ the uncertainty map when segmenting a portion of the patient image displaced from the metal object using model-based segmenting;
- compute external and internal energies to be applied to each triangle of a model surface using respective best features and weights, wherein the internal energy increases and the external energy decreases as a function of an increase in the likelihood of metal contamination associated with each corrected voxel; and
- model the internal energy as:

$$E_{int} = \sum_{e=1}^{e=N_{edges}} (\vec{x}_e - sR\vec{x}_e^0)^2,$$

wherein $E_{int}$ is internal energy, $N_{edges}$ is the number of edges in the mesh, $\vec{x}_e$ is a vector representing edge e, s is a mean mesh scaling factor, R is the mean mesh rotation vector, and $\vec{x}_e^0$ is a mean mesh vector representing edge e.

10. The processor according to claim 9, further configured to overlay a mesh model on the patient image and align corresponding features in the model and the patient image.

11. The processor according to claim 10, further configured to apply external forces to the mesh model to pull one or more features on the surface of the mesh model inward toward corresponding image features.

12. The processor according to claim 11, further configured to apply internal forces to the mesh model surface to pull one or more features outward toward corresponding image features.

13. The processor according to claim 12, further configured to weight the internal forces as a function of a degree to which voxels in the one or more features are affected by the metal.

14. The processor according to claim 9, wherein the model-based segmenting includes:
- assigning a best feature and a feature weight to each triangle of a plurality of triangles that comprise the surface of the mesh model;
- modeling the external an internal energies as mathematical equations;
- solving the mathematical equations; and
- updating the shape of the mesh model as a function of the equation solutions.

15. The processor according to claim 14, further configured to model the external energy as:

$$E_{ext} = \sum_{t=1}^{t=N_\Delta} r(\hat{x}_t) w_t (\tilde{x}_t - \hat{x}_t)^2,$$

wherein $E_{ext}$ is external energy, $N_\Delta$ is the number of triangles in the mesh surface, $r(\hat{x}_t)$ represents the reliability of the external energy and is spatially variant, $w_t$ is the feature strength of a triangle t, $\tilde{x}_t$ is the coordinates of the best feature for triangle t, and $\hat{x}_t$ is the coordinates of the center of triangle t.

16. The processor according to claim 14, further configured to iteratively perform the acts of claim 14, until the mesh model conforms to the patient image.

17. The method of claim 9, further including reducing metal artifacts in the patient image.

18. A system that facilitates model-based segmentation using uncertainty maps, including:
- a processor configured to:
  - generate patient image data;
  - reconstruct the patient image data into a 3D patient image;
  - detect metal artifacts in one or more voxels in the 3D patient image;
  - generate an uncertainty map with interpolated data that reduces the metal artifacts, wherein the uncertainty map indicates a likelihood of metal contamination of corrected voxels representing boundary surfaces of one or more remote organs in other parts of the 3D patient image;
  - weight features associated with regions of a surface of a mesh model; and
  - segment the 3D patient image using model-base segmentation to conform the mesh model to the 3D patient image.

19. A method of performing model-based segmentation, comprising:
- generating, via a diagnostic imaging device, a diagnostic image of an organ or region of a subject, which image has metal artifacts;
- selecting a model of the imaged organ or region;

applying, via a processor, a first energy on the model, which urges the model to hold its initial shape;

applying, via a processor, a second energy on the model, which urges the model to deform into alignment with corresponding interfaces in the diagnostic image;

on an image voxel by image voxel basis, adjusting the first and second energies in accordance with the degree of metal artifacting, such that the magnitude of the first energy relative to the second energy increases for voxels with a higher degree of metal artifacting, and the magnitude of the second energy relative to the first force increases for voxels with a lower degree of metal artifacting; and computing the external and internal energies to be applied to a model surface using respective best features and weights; and model the internal energy as:

$$E_{int} = \sum_{e=1}^{e=N_{edges}} \left(\vec{x}_e - sR\vec{x}_e^0\right)^2,$$

wherein $E_{int}$ is internal energy, $N_{edges}$ is the number of edges in the mesh, $\vec{x}_e$ is a vector representing edge e, s is a mean mesh scaling factor, R is the mean mesh rotation vector, and $\vec{x}_e^0$ is a mean mesh vector representing edge e.

20. A system for image segmentation in the presence of metal artifacts, including:

a model generator that receives patient image data and stores trained models of anatomical structures;

a voxel analyzer that determines whether metal artifacts are present in one or more voxels in the patient image data;

a processor that generates an uncertainty map, which indicates a likelihood of metal contamination for corrected voxels representing surface boundaries in the patient image, without changing the patient image data; and a segmentation tool that:
  conforms a trained model of an anatomical structure corresponding to the patient image by applying external and internal energies to each triangle of the model surface;
  segments the patient image using a model-based segmentation technique; and
  evaluates the uncertainty map derived by the processor;

wherein the internal energy is modeled as:

$$E_{int} = \sum_{e=1}^{e=N_{edges}} \left(\vec{x}_e - sR\vec{x}_e^0\right)^2,$$

wherein $E_{int}$ is internal energy, $N_{edges}$ is the number of edges in the mesh, $\vec{x}_e$ is a vector representing edge e, s is a mean mesh scaling factor, R is the mean mesh rotation vector, and $\vec{x}_e^0$ is a mean mesh vector representing edge e.

* * * * *